United States Patent

Beavers

Patent Number: 6,147,233
Date of Patent: Nov. 14, 2000

[54] PROCESS FOR THE PREPARATION OF 3-METHYLTETRAHYDROFURAN

[75] Inventor: William Anthony Beavers, Longview, Tex.

[73] Assignee: Eastman Chemical Company, Kingsport, Tenn.

[21] Appl. No.: 09/489,188

[22] Filed: Jan. 20, 2000

[51] Int. Cl.[7] .................................................. C07D 307/08
[52] U.S. Cl. .......................................... 549/508; 549/509
[58] Field of Search ...................................... 549/508, 509

[56] References Cited

U.S. PATENT DOCUMENTS

| | | |
|---|---|---|
| 3,859,369 | 1/1975 | Copelin . |
| 3,932,468 | 1/1976 | Kurkov . |
| 4,590,312 | 5/1986 | Ernst . |
| 4,772,729 | 9/1988 | Rao ......................... 549/326 |
| 4,879,420 | 11/1989 | Ernst . |
| 5,391,771 | 2/1995 | Weyer et al. ........................... 549/326 |
| 5,536,854 | 7/1996 | Weyer et al. . |
| 5,856,527 | 1/1999 | Beavers . |
| 5,912,364 | 6/1999 | Beavers ................... 549/429 |
| 5,945,549 | 8/1999 | Beavers . |

FOREIGN PATENT DOCUMENTS

| | | |
|---|---|---|
| 727422 | 8/1996 | European Pat. Off. . |
| 747373 | 12/1996 | European Pat. Off. . |
| 8-217708 | 8/1996 | Japan . |
| 8-217770 | 8/1996 | Japan . |
| 8-217771 | 8/1996 | Japan . |
| 8-291158 | 11/1996 | Japan . |

OTHER PUBLICATIONS

G. J. Baumgartner et al, Reactions of Furan Compounds, XVII. Pyrolysis of Tetrahydrofurfuryl Esters to Methyl Propenyl Ketone, J. Amer. Chem. Soc., vol. 81, 2440–2442 (1959).

Primary Examiner—Joseph K. McKane
Assistant Examiner—Sonya N Wright
Attorney, Agent, or Firm—Michael J. Blake; Harry J. Gwinnell

[57] ABSTRACT

Disclosed is a process for the preparation of 3-methyltetrahydrofuran (3-MeTHF) from 3-(hydroxymethyl)tetrahydrofuran (3-HOMeTHF) by a plurality of process steps comprising (1) esterifying 3-HOMeTHF to produce a carboxylate ester of 3-HOMeTHF, (2) pyrrolyzing the carboxylate ester to produce 3-methylenetetrahydrofuran (3-methyleneTHF), and (3) hydrogenating the 3-methyleneTHF to produce 3-MeTHF. The 3-MeTHF produced in accordance with the present invention is useful as an industrial solvent and as a monomer in the manufacture of polymers such as elastomers.

12 Claims, No Drawings

PROCESS FOR THE PREPARATION OF 3-METHYLTETRAHYDROFURAN

INTRODUCTION

This invention pertains to a novel process for the preparation of 3-methyltetrahyd rofuran (3-MeTHF) from 3-hydroxymethyltetrahydrofuran (3-HOMeTHF). More specifically, this invention pertains to a multi-step process comprising the steps of (1) esterifying 3-HOMeTHF to produce a carboxylate ester of 3-HOMeTHF, (2) pyrrolyzing the carboxylate ester to produce 3-methylenetetrahydrofuran (3-methyleneTHF), and (3) hydrogenating the 3-methyleneTHF to produce 3-MeTHF. The 3-MeTHF produced in accordance with the present invention is useful as an industrial solvent and, more importantly, as a monomer in the manufacture of polymers such as elastomers.

BACKGROUND OF THE INVENTION

3-MeTHF has been produced in commercial quantities by the high pressure hydrogenation of citraconic anhydride and some of its derivatives according to the procedures disclosed in U.S. Pat. No. 5,536,854 and Published Japanese Patent Application (Kokai) 08-217,771. Since citraconic acid is formed from citric acid or, more economically, as a minor by-product, during maleic anhydride production, these routes to 3-MeTHF are expensive and use a starting material which is not plentiful.

Processes for the production of 3-MeTHF based on less expensive precursors and precursors independent of the production of other materials have been developed. Thus, U.S. Pat. No. 3,932,468, describes a process for isomerizing isoprene monoepoxide into 4-methyl-2,3-dihydrofuran using a nickel and hydrohalic acid catalyst. Although the hydrogenation of 4-methyl-2,3-dihydrofuran into 3-MeTHF is relatively simple, the synthesis of the starting material, isoprene monoepoxide, is not. For example, the preparation of isoprene monoepoxide would require the use of classical (and expensive) epoxide manufacturing techniques such as the use of halohydrins or co-oxidation with aldehydes. Japanese Published Patent Application (Kokai) JP 08-291, 158 describes another method for preparing 3-MeTHF in which propylene is converted into 2-methylsuccinate esters by a double oxidative carbonylation in the presence of an alcohol. Although the reductive cyclization of the 2-methylsuccinate esters to 3-MeTHF is facile, the double oxidative carbonylation reaction usually gives limited yields of the dicarbonylated products and requires expensive, reactive solvents to keep the reagents anhydrous.

Another method for the synthesis of 3-MeTHF is disclosed in U.S. Pat. No. 3,859,369 and comprises the hydroformylation of 2-buten-1,4-diol into 2-methyl-1,4-butanediol which is converted to 3-MeTHF by acid catalysis. U.S. Pat. Nos. 4,590,312 and 4,879,420 describe the conversion of 4-hydroxybutyraldehyde and its immediate precursor, 2-buten-1,4-diol, into 3-MeTHF by reductive alkylation with formaldehyde followed by acid catalyzed cyclization. In each case, the products were mixtures of 3-MeTHF and tetrahydrofuran. This situation occurred in the hydroformylation process because isomerization accompanied the hydroformylation, limiting the yield of 3-MeTHF by forming a tetrahydrofuran precursor. In the reductive alkylation processes, the intermediate products as well as the starting materials could form alcohols by hydrogenation. Only those hydrogenations occurring after an initial aldol condensation of the reactants with formaldehyde could form 3-MeTHF. All other hydrogenations gave tetrahydrofuran or other byproducts.

The preparation of 3-MeTHF also is disclosed in Published European Patent Application EP 727 422 and involves the hydrocyanation of methacrylate esters. A series of hydrolyses and esterifications forms a diester which may be reductively cyclized to 3-MeTHF using an acidic, copper chromite catalyst. In this case, not only were the starting materials expensive (although not as expensive as the citraconic anhydride derivatives), but the synthesis required four steps. Japanese Published Patent Application (Kokai) JP 08-217,708 describes a process for producing 3-MeTHF by the hydroformylation of methacrylate esters to form mixtures of the α-formylisobutyrate and the β-formylisobutyrate esters using synthesis gas. Japanese Published Patent Application (Kokai) JP 08-217,770 discloses a similar hydroformylation using methyl formate as the C-1 source. In both of these hydroformylation processes, hydrogenation of the resulting β-formylisobutyrate ester over a copper chromite catalyst gave 3-MeTHF. One further hydroformylation route reported in Published European Patent Application Publication EP 747,373 consists of (1) the hydroformylation of isobutenyl alcohol (2-methyl-2-propen-1-ol) to form 4-hydroxy-3-methylbutyraldehyde which (2) was readily hydrogenated with nickel catalysts to 2-methyl-1,4-butanediol and which (3) was cyclized to 3-MeTHF by acid catalysis.

U.S. Pat. No. 5,856,527 discloses a process for the preparation of 3-alkyltetrahydrofurans by a two-step process wherein 2,3-dihydrofuran is reacted with an acetal to form an intermediate compound which may be converted to a 3-alkyltetrahydrofuran by contacting the intermediate with hydrogen in the presence of a catalystic amount of a Group VIII noble metal or rhenium and a strong catalyst. U.S. Patent discloses a two-step process wherein (1) 2,3-dihydrofuran is reacted with a trialkyl orthoformate in the presence of an acidic catalyst to produce 2-alkoxy-3-dialkoxymethyl)-tetrahydrofuran and (2) the intermediate is contacted with hydrogen in the presence of a catalyst system comprising a Group VIII noble metal or rhenium and a strong acid to convert the intermediate to a mixture of 3-MeTHF and 3-HOMeTHF.

U.S. Pat. No. 5,912,364 discloses the preparation of 3MeTHF by contacting 3-formyltetrahydrofuran with hydrogen in the presence of a catalyst system comprising a Group VIII noble metal or rhenium and a strong acid under hydrogenolysis conditions of temperature and pressure. The disclosed process typically produces a mixture of 3-MeTHF and 3-HOMeTHF. This patent also discloses processes for the preparation of 3-formyltetrahydrofuran by contacting 2,5-dihydrofuran with synthesis gas comprising carbon monoxide and hydrogen in the presence of a rhodiumphosphorus catalyst system according to known hydroformylation procedures. U.S. Pat. No. 5,945,549 discloses a process for the recovery of formyltetrahydrofurans (FTHF's) produced by the rhodium-catalyzed hydroformylation of 2,3-dihydrofuran wherein the FTHF's are recovered as an equilibrium mixture of 2- & 3-FTHF and their hydrates, 2- and 3-[di(hydroxy)methyl]tetrahydrofuran from a hydroformylation product solution comprising a rhodium catalyst, 2- and 3-FTHF and an organic hydroformylation solvent obtained as a liquid product take-off from a hydroformylation process wherein 3-FTHF is produced by the hydroformylation of 2,5-dihydrofuran. These known methods for the production of 3-MeTHF starting with 3-formyltetrahydrofuran suffer from one or more disadvantages such as low reaction yields, the co-production of other compounds which have limited utility and/or the use of corrosive aicds.

BRIEF SUMMARY OF THE INVENTION

The present invention is based on the discovery that 3-HOMeTHF can be converted to 3-MeTHF by means of a novel combination of process steps. The present invention provides a process for the preparation of 3-MeTHF by the steps comprising (1) contacting 3-HOMeTHF with a carbonyl esterifying compound or agent under esterification conditions to produce a carboxylate ester of 3-HOMeTHF; (2) heating the carboxylate ester of step (1) under pyrrolysis conditions to convert the carboxylate ester of 3-HOMeTHF to 3-methyleneTHF; and (3) contacting the 3-methyleneTHF with hydrogen in the presence of a hydrogenation catalyst under hydrogenation conditions of temperature and pressure. This combination of process steps is particularly unique since each step gives excellent yields of desired product with the ultimate 3-MeTHF product being obtained in a yields of 90% or greater based on the HOMeTHF starting material.

DETAILED DESCRIPTION

The first step of my novel process involves contacting 3-HOMeTHF with a carbonyl esterification or acylating agent under esterification conditions to produce a carboxylate ester of 3-HOMeTHF. The carboxylic esterification or acylating agent may be selected from a broad variety of carboxylic compounds such as ketenes and carboxylic acids, carboxylic anhydrides, carboxylic acid halides and carboxylic acid esters. Examples of the carboxylic acids which may be used include aliphatic monocarboxylic and dicarboxylic acids containing up to about 20 carbon atoms such as formic, acetic, propionic, 2-methylpropionic, butyric, 2-methylbutyric, 2-ethylbutyric, 3-methylbutyric, pentanoic, 2-methylpentanoic, 3-methylpentanoic, 4-methylpentanoic, 2-ethylpentanoic, 3-ethylpentanoic, 2-propylpentanoic, hexanoic, 2-methylhexanoic, 3-methylhexanoic, 4-methylhexanoic, 5-methylhexanoic, 2-ethylhexanoic, 2-ethyl-2-hexenoic, 3-ethylhexanoic, 4-ethylhexanoic, 2-propylhexanoic, 2-butylhexanoic, octanoic, decanoic, dodecanoic, oxalic, malonic, succinic, glutaric, adipic, maleic, fumaric, and succinic acids; cycloaliphatic carboxlic acids containing 5 to 10 carbon atoms such as cyclopentylcarboxylic and cyclohexylcarboxylic; aromatic carboxylic and dicarboxylic acids containing 6 to 20 carbon atoms such as benzoic, 2-methylbenzoic, 3-methylbenzoic, 4-methylbenzoic, 4-methoxybenzoic, naphthalene-2-carboxylic, naphthalene-3-carboxylic, biphenyl-2-carboxylic, biphenyl-3-carboxylic, biphenyl4-carboxylic, 1,2-, 1,3-, and 1,4-benzenedicarboxylic acids. The anhydrides and acid halides of the above carboxylic acids also may be used as well as esters thereof, e.g., alkyl and aryl esters of the carboxylic acids. The particular reaction conditions and parameters, such as temperature, catalyst, the presence of water and/or organic solvents, etc., involved in step (1) which will give the best results may be determined by those skilled in the art. Carboxylic acids containing 2 to 4 carbon atoms, and especially acetic acid, represent the preferred carbonyl esterification agents or compounds. The preferred carboxylic acids are thermally stable and, thus, are not decomposed, or decomposed to a significant degree, in the pyrolysis step of the present process. This thermal stability confers two benefits: (i) the carboxylic acid may be recovered from the pyrolysis step and recycled and (ii) no carboxylic acid decomposition products need to be removed from the process.

Step (1) may be carried out by heating 3-HOMeTHF and a carbonyl esterfication compound in an esterfication zone at a temperature in the range of about −50 to 300° C. in the absence or presence of an esterification catalyst. For example, an acidic or, preferably, a basic catalyst such as pyridine, sodium acetate, potassium acetate, sodium methoxide, potassium ethoxide and the like may facilitate the esterification when using a carboxylic acid halide, e.g., an acid chloride, bromide, fluoride or iodide, a carboxylic acid anhydride or a carboxylic acid ester. The mole ratio of the carbonyl esterfication agent: 3-HOMeTHF normally is at least 1:1 and preferably in the range of about 1.05:1 to 50:1. When using acetic acid as the estrification agent, the most preferred acetic acid: 3-HOMeTHF ratio is 1.1:1 to 3:1. The esterification may be carried out in an inert organic solvent under substantially anhydrous conditions when the esterfication agent is an anhydride or an acid halide. Examples of such inert (nonreactive) organic solvents include aromatic hydrocarbons such as benzene, toluene, and the xylenes; ethers such as tetrahydrofuran, tetrahydropyran, 1,3-dioxane, 1,4-dioxane, anisole, diphenylether, diethylether, and diisopropylether; and, halogenated hydrocarbons such as chloroform, dichloromethane, chlorobenzene, dichloroethane, trichloroethane, and the chlorofluorocarbons. Such an inert solvent may be used when the carboxylic acid employed as the esterification agent has limited or low solublity in the 3-HOMeTHF. The 3-HOMeTHF advantageously is used as a water solution obtained by the catalytic hydrogenation of the mixture of formyltetrahydrofuran and hydrates thereof produced as described in U.S. Pat. No. 5,945,549.

The esterification preferably is performed using a carboxylic acid and an apparatus which permits water to be removed from the esterfication zone. In a preferred embodiment, the esterification is carried out utilizing reactive distillation wherein 3-HOMeTHF and a carboxylic acid such as acetic acid are fed to a column equipped with trays and/or packing material to promote intimate contact of the reactants and/or to a distillation base pot. Water is removed from the upper section or top of the column and a carboxylate ester of 3-HOMeTHF or, more typically, a mixture of the carboxylate ester of 3-HOMeTHF, unreacted carboxylic acid, e.g., acetic acid, unreacted 3-HOMeTHF, and a small amount of side products is removed from the distillation base pot. I have found that both 3-HOMeTHF and a preferred carboxylic acid such as acetic acid are substantially inert to subsequent processing conditions. Thus, both materials may be recovered from subsequent process steps and recycled to the first step of the process. In the preferred reactive distillation mode of operation using acetic acid to produce 3-(acetoxymethyl)tetrahydrofuran, the temperature in the distillation base pot and at the base of the column is in the range of about 120 to 210° C. and the temperature at the top of the column is in the range of about 99 to 101° C. The 3-HOMeTHF reactant used in the esterification step preferably is used in the form of a 10 to 90 weight percent, most preferably 40 to 60 weight percent, solution of 3-HOMeTHF in water.

The 3-HOMeTHF used in the esterfication process may be obtained by hydrogenating 3-formyltetrahydrofuran in the presence of a hydrogenation catalyst such as Raney nickel or a supported nickel catalyst, e.g., about 20 to 80 weight percent nickel deposited on a catalyst support material such as activated charcoal, graphite, alumina, silica, silicaalumina, zirconia, titania, zinc oxide, various clays or various zeolites. The 3-formyltetrahydrofuran material may be in the form of an aqueous solution of the 3-formyltetrahydrofuran and its hydrate, e.g., a 10 to 90 weight percent, preferably 40 to 60 weight percent, solution of 3-formyltetrahydrofuran/hydrate in water, obtained in accordance with the process described in U.S. Pat. No. 5,945,549. The 3-formyltetrahydrofuran material may contain a minor amount of 2-formyltetrahydrofuran formed as a by-product of the hydroformylation of 2,5-dihydrofuran. Normally, the 2-isomer: 3-isomer mole ratio does not exceed 0.05:1. The hydrogenation of 3-formyltetrahydrofuran may be carried out at a temperature of about 25 to 250° C. and a pressure of about 1 to 400 bar absolute (bara). The preferred hydrogenation conditions are a temperature in the range of about 90 to 150° C. and a pressure in the range of about 10 to 50 bara. To achieve high selectivity of 3-HOMeTHF, it also is preferred that the hyrogenation be carried out using a 0.01 to 50 weight percent solution of 3-formyltetrahydrofuran in an inert solvent, preferrably a 0.1 to 10 weight percent solution of 3-formyltetrahydrofuran in an inert solvent selected from water, 3-HOMeTHF or a mixture thereof.

In the second step of the process of the present invention, the carboxylate ester of 3-HOMeTHF is pyrolzed to convert it to 3-methyleneTHF. The pyrolysis is carried out by heating the 3-HOMeTHF carboxylate ester in a pyrolysis zone at a temperature in the range of about 380 to 510° C. for a period of time sufficient to convert the ester compound to 3-methyleneTHF, typically for a period of about 0.1 to 20 seconds, preferably about 1 to 10 seconds. Step (2) may be carried out using a heated, tubular reactor containing an inert, inorganic, ceramic or metallic packing material in the form of chips, particles and/or shards to provide a surface for vaporizing and transmitting the thermal energy to the 3-HOMeTHF carboxylate ester for the pyrrolysis reaction. Examples of suitable packing materials include Vitreous silica, Vicor glass and Pyrex glass. Generally, the feed to the pyrolysis zone should be free, or substantially free, of any materials used or co-produced in the first step which will affect the quality of the pyrolysis product. Certain solvents, esterification catalysts or esterification co-products may react in the pyrolysis zone to adversely affect the desired high yield of the 3-methyleneTHF. For example, benzene or toluene solvent may react with carboxylic acid typically present to produce an aromatic ketone, e.g., the reaction of benzene or toluene with acetic acid to produce acetophenones. Any hydrogen halide present as the result of using an acid halide as the esterification agent may isomerize the 3-methyleneTHF into 3-methyl-4,5-dihydrofuran and then catalyze the polymerization of this latter compound.

The contact time employed in step (2), i.e., the period of time that the ester reactant and 3-methyleneTHF product are heated at a temperature in the range of 380 to 510° C. in the pyrolysis zone, can be varied significantly depending, for example, on other factors such as the temperature and the particular apparatus used. Generally, the contact time will be in the range of about 0.1 to 20 seconds, preferably about 1 to 10 seconds. To achieve a selectivity to the desired 3-methyleneTHF, it is preferred that step (2) is operated in a manner that gives a conversion of the 3-HOMeTHF carboxylate ester of less than 85 mole percent, preferably a conversion of the 3-HOMeTHF carboxylate ester of about 35 to 85 mole percent. The gaseous product obtained from the pyrolysis zone normally is condensed and, after an optional filtration to remove carbonaceous or other insoluble material, used without purification in the third step of the process. The 3-methyleneTHF produced in step (2) may be recovered as a solution in the liquid carboxylic acid co-product of the pyrolysis reaction and/or as a solution in any inert organic solvent utilized in step (2). For example, when the 3-HOMeTHF carboxylate ester feed to the pyrolysis zone is 3-(acetoxymethyl)tetrahydrofuran, the condensed product from the pyrolysis zone is a solution of 3-methyleneTHF in acetic acid which may be used in the subsequent hydrogenation reaction.

I have found that the 3-methyleneTHF derived from the 3-HOMeTHF carboxylate ester is relatively stable and inert to the pyrolysis conditions. However, 2-methyleneTHF derived from any 2-HOMeTHF carboxylate ester present is very reactive and, advantageously, is removed from the process by decomposition within the pyrolysis zone. This advatageous result is consistent with the observations of G. J. Baumgartner and C. L. Wilson reported in *Reactions of Furan Compounds. XVII. Pyrolysis of Tetrahydrofurfuryl Esters to Methyl Propenyl Ketone*, J. Amer. Chem. Soc., 81, 2440 (1959).

In the third step of the present invention, 3-methyleneTHF is converted to 3-MeTHF by contacting the 3-methyleneTHF with hydrogen in the presence of a hydrogenation catalyst under hydrogenation conditions of temperature and pressure. The hydrogenation of 3-methyleneTHF may be carried out at a temperature of about −80 to 200° C. and a pressure of about 0.1 to 100 bara. The preferred hydrogenation conditions are a temperature in the range of about 25 to 100° C. and a pressure in the range of about 1 to 50 bara.

The hydrogenation catalyst employed in step (3), in general, is not critical and may be selected from the various hydrogenation catalysts, particularly those commonly used for the hydrogenation of olefinic compounds. Examples of hydrogenation catalysts include chromium, rhenium, copper and the Group VIII metals. These metals may be used in the form of oxides or in their reduced form, e.g., as finely divided metals, and, optionally, in the form of metals deposited on a catalyst support material, e.g., silica, alumina, titania, zirconia, zinc oxide, charcoal, graphite and similar known support materials. The step (3) hydrogenation catalyst preferably is selected from supported catalysts comprising about 0.01 to 25, preferably about 1 to 10, weight percent palladium, platinum or rhodium deposited on a catalyst support material. The catalyst most preferably is selected from palladium and rhodium catalysts, especially supported catalysts comprising about 1 to 10 weight percent palladium deposited on charcoal or carbon.

The amount or concentration of the hydrogenation catalyst which is catalytically effective to convert essentially all of the 3-methyleneTHF to 3-MeTHF can be varied significantly depending upon the particular catalyst metal used, the form in which it is used, the mode in which the process is operated and other process variables such as temperature, pressure and residence time. For example, the amount of catalyst metal present may be from 0.000001 to more than 100 gram atoms metal per mole of methyleneTHF present. However, when using certain modes of operation the amount of catalyst present per unit of reactant is virtually impossible to define. For example, the process may be operated continuously in a trickle bed manner wherein a liquid stream of methyleneTHF or a solution thereof is flowed (or "trickled") over a bed of catalyst in the presence of hydrogen under hydrogenation conditions of temperature and pressure to produce 3-MeTHF. In batch operation, the amount of hydrogenation catalyst metal present preferably is about 0.001 to 50, most preferably 0.1 to 10, gram atoms per mole of 3-methyleneTHF present.

The 3-methyleneTHF normally is used in conjunction with a solvent in step (3). The solvent may be acetic acid or other liquid carboxylic acid co-produced in the pyrolysis step. Other material which may be used as hydrogenation solvents include alkanols containing up to about 6 carbon atoms, especially, methanol, ethanol, and 1- and 2-propanol; hydrocarbons such as benzene, toluene, and the xylenes; ethers such as tetrahydrofuran, tetrahydropyran, 1,3-dioxane, 1,4-dioxane, anisole, diphenylether, diethylether, and diisopropylether; and, halogenated hydrocarbons such as chloroform, dichloromethane, chlorobenzene, dichloroethane, trichloroethane, and the chlorofluorocarbons. Because of their catalyst wetting characteristics, the use of methanol and ethanol as solvents or co-solvents can enhance the catalytic hydrogenation of 3-methyleneTHF. However, certain solvents, e.g., methanol and ethanol, form azeotropes (constant boiling mixtures) with 3-MeTHF, which can require special procedures in the final distillative purification of the 3-MeTHF obtained from the step (3) hydrogenation procedure. For example, methanol/3-MeTHF mixtures obtained by the distillation of a methanol/3-MeTHF azeotrope at 64° C. may be combined with toluene and heated to distill a methanol/toluene azeotrope at 62° C. and, when all of the methanol has been removed, the 3MeTHF distills at 86.6° C.

An embodiment of the present invention which is especially preferred involves the steps of (1) contacting an aqueous solution of 3-HOMeTHF with acetic acid in an esterification zone using a reactive distillation apparatus comprising a distillation base pot and a distillation column wherein 3-HOMeTHF and acetic acid are fed to the reactive distillation apparatus, water is removed as a vapor from the upper section or top of the distillation column and a liquid a mixture comprising 3-(acetoxymethyl)THF, HOMeTHF and acetic acid is removed as a liquid from the distillation base pot of the esterification zone; (2) heating the liquid mixture from step (1) under pyrrolysis conditions to convert the 3-(acetoxymethyl)THF to 3-methyleneTHF and condensing and recovering the 3-methyleneTHF as a solution in acetic acid; and (3) contacting the solution of 3-methyleneTHF in acetic acid with hydrogen in the presence of a hydrogenation catalyst under hydrogenation conditions of temperature and pressure. The concentration of the 3-methyleneTHF in the acetic acid solution recovered from step (2) may range from about 5 to 50 weight percent 3-methyleneTHF in acetic acid depending largely on the molar ratio of acetic acid to 3-HOMeTHF used in the esterification step (1) and the conversion of the carboxylate ester during the pyrolysis step (2).

The crude product obtained from the 3-step process provided by the present invention typically contains about 5 to 50 weight percent 3-MeTHF, about 10 to 70 weight percent 3-acetoxymethylTHF, about 30 to 60 weight percent acetic acid, and up to about 5 weight percent of a mixture of low boilers, high boilers, water, and other materials. 3-MeTHF can be recovered from this crude product using two fractional distillations. In the first distillation, 3-MeTHF, the low boilers, and much of the water is vaporized and removed overhead. The distillation residue (column or base underflow) comprises 3-acetoxymethylTHF, acetic acid, the high boilers, the rest of the water, and other materials. The overhead distillate is subjected to a second fractional distillation and the base underflow stream may be recycled to preceding steps of the overall manufacturing process.

In the second fractional distillation the low boilers are vaporized and removed as distillate. These low boilers consist mostly of hydrocarbon decomposition products of the THF derivatives and acetone from the decomposition of the acetic acid. The water is removed from the distillation column at a lower plate as an azeotrope with 3-MeTHF and is fed to a decanter. 3-MeTHF may be recovered from the top layer for recycling to the middle of this column and would recover the bottom water layer for recycling to the first distillation column. In this way, the final product is dehydrated with the water eventually being forced through the base overflow of the first column to recycle along with the other recycle components. The 3-MeTHF product is recovered as the column or base underflow. This second distillation typically provides 99.90+ percent pure 3-MeTHF as a base product.

The process of the present invention is further illustrated by the following example. As used herein, the percent conversion of a reactant is:

$$\frac{\text{Moles Reactant Converted}}{\text{Moles Reactant Fed}} \times 100$$

and the percent selectivity to a particular compound:

$$\frac{\text{Moles Reactant Converted to the Compound}}{\text{Moles Reactant Converted}} \times 100$$

EXAMPLE

Step (1)-Esterification

To a 5-L, round-bottom flask equipped with a thermometer in a thermowell, an addition funnel, and topped with a 30 plate Oldershaw fractional distillation column were charged 2817.4 grams of 99.98 percent pure 3-HOMeITHF (27.580 moles), 2053 milliliters of glacial acetic acid (d=1.0491, 2153.8 grams, 35.865 moles), and 20 carborundum boiling chips. The initial molar [HOAc]/[HOMeTHF] ratio was 1.3002. The reaction began by heating the contents to reflux, which initially occurred at 149.7° C. in the base pot. The temperature in the distillation head was 100.0° C. With a reflux ratio of 4:1, the reaction continued removing the water produced in the acetylation to drive the reaction to completion. The temperature in the base distillation pot dropped to 138.4° C. over the next three hours as the distillation was not able to keep up with the water produced by the esterification. During this time, a total of 167 milliliters of water (9.27 moles) distilled overhead representing a 33.6 percent conversion of the starting alcohol. From this low point, the temperature climbed steadily over the next 14 hours to 186.0° C. During this time, a total of 473 milliliters of water (26.3 moles) distilled overhead representing a 95.2 percent conversion of the starting alcohol. Throughout this early part of the reaction, the temperature in the distillation head stayed at 100.0° C. But as the conversion of the starting alcohol exceeded 95 percent, it was necessary to increase the reflux ratio to 15:1 to prevent acetic acid from co-distilling. Over the next 7 hours, the base temperature increased to 189.2° C. and a total of 487 milliliters of water distilled representing a conversion of 98.0 percent. At this point, the temperature in the distillation head began to rise reaching 118.5° C. after 4 hours as the base temperature climbed to 204.0° C. and 405 milliliters of additional distillate collected. Water analysis showed this distillate to contain 1.45 weight percent water or 6.16 grams representing an additional 1.2 percent conversion or a total conversion of 99.2 percent. Gas chromatographic analysis showed the material remaining in the reaction flask contained 1.99 percent acetic acid, 0.78 percent 3-HOMeTHF, 0.08 percent low boilers, and 97.15 percent 3-acetoxymethylTHF. Based on these values, the selectivity to 3-acetoxymethylTHF was 99.92 percent. The crude, undistilled product was used directly in the step (2) pyrolysis reaction appearing as a light amber solution.

Step (2)-Pyrolysis

The pyrolysis zone or reactor consisted of a tube of Vicor fused quartz having a diameter of 25.4 mm (1 inch) filled with Vicor glass shards. An 81.3 cm (32 inch) section of the tube was heated by means of a Lindberg three stage electical furnace. The total volume of the pyrolysis reactor was 190 cc. The feed material used in the pyrolysis was the product of the esterification described above. The reaction configuration fed the pyrolysis feed material from a 1-liter glass tank through a bellows pump to the top of the reactor where it was combined with nitrogen co-feed and sent through the reactor. The material coming from the base of the reactor was condensed and collected in either of two traps, an air-cooled trap for most material and a dry-ice cooled trap for the low boiling material.

The experiment started with 950 milliliters of 3-acetoxymethylTHF (base product from 3-HOMeTHF acetylation consisting of 97.2 weight percent 3-AcOMeTHF) pumped into the reactor over 5.45 hours with 128 cc/minute of dry nitrogen co-feed. This rate corresponds to a contact time of 4.3 seconds at a conversion of 81 percent and a temperature of 450° C. The material collected in the traps amounted to 932 milliliters in the air cooled trap and an additional 17 milliliters in the dry ice cooled trap. The 932 mL collected in the air cooled trap consisted approximately of 43.94 weight percent 3-methyleneTHF, 0.45 weight percent 3-methyl-4,5-dihydrofuran, 0.03 weight percent other 3-methyldihydrofuran isomers, 18.27 weight percent 3-acetoxymethylTHF, 32.95 weight percent acetic acid, 3.55 weight percent other low boilers, and 0.81 weight percent other high boilers. Gas chromatographic analysis showed a conversion of 3-acetoxymethylTHF of 81.2 percent and a selectivity to 3-methyleneTHF of 95.43 percent and a selectivity to 3-methyl-4,5-dihydrofuran of 0.98 percent. The remainder of the material balance was a mixture of hydrocarbons (butanes, butenes, pentanes, pentenes, etc.), carbonyl compounds (acetone and formaldehyde) and alcohols (butanols, pentanols, etc.).

Step (3)-Hydrogenation

About 1 liter of crude product obtained from the air cooled and dry ice cooled traps in Step (2) was pumped into a 2-liter Parr autoclave containing 25.5 grams of 5 percent palladium on activated charcoal catalyst and 500 milliliters of solvent (either acetic acid or a mixture of acetic acid and methanol). The conditions within the autoclave were a hydrogen pressure of 35.5 bara (500 pounds per square inch), a temperature of 50° C. and a stirring rate of 1600 revolutions per minute. During the addition over a period of 120 minutes, the hydrogen uptake was about 98 percent of the theoretical amount and the uptake stopped within 2 minutes of completing addition of the organic feed. To ensure complete reaction, the heating and stirring continued for 30 minutes afterwards followed by a 30-minute treatment at 100° C. at 35.5 bara hydrogen pressure and 1600 RPM stirring rate. The only parameter varied in this reaction was the solvent, which included either methanol or acetic acid. The difference in the results obtained from experiments with the two solvents was negligible. The conversion of the 3-methyleneTHF exceeded 99.9% and the average selectivity to 3-MeTHF exceeded 98%.

The 3-step process produces 3-MeTHF from 3-HOMeTHF in an overall yield of 94.9%. This value is based on yields 99.92 percent for the acetylation of 3-HOMeTHF to 3-AcOMeTHF, 96.60 percent for the pyrolysis of 3-AcOMeTHF to 3-methyleneTHF, and 98.32 percent for the hydrogenation of 3-methyleneTHF to 3-MeTHF.

The invention has been described in detail with particular reference to preferred embodiments thereof, but it will be understood that variations and modifications can be effected within the spirit and scope of the invention.

I claim:

1. Process for the preparation of 3-methyltetrahydrofuran (3-MeTHF) by the steps comprising (1) contacting 3-(hydroxymethyl)tetrahydrofuran (3-HOMeTHF) with a carbonyl esterification compound under esterification conditions to produce a carboxylate ester of 3-HOMeTHF; (2) heating the carboxylate ester of step (1) under pyrrolysis conditions to convert the carboxylate ester of 3-HOMeTHF to 3-methylenetetrahydrofuran (3-methyleneTHF); and (3) contacting the 3-methyleneTHF with hydrogen in the presence of a hydrogenation catalyst under hydrogenation conditions of temperature and pressure.

2. Process according to claim 1 wherein step (1) comprises contacting 3-HOMeTHF with a carboxylic acid containing 2 to 4 carbon atoms at a temperature of about 120 to 210° C. in an esterification zone using apparatus which permits water to be removed from the esterification zone to produce a carboxylate ester of 3-HOMeTHF.

3. Process according to claim 1 wherein step (1) comprises contacting 3-HOMeTHF with a carboxylic acid containing 2 to 4 carbon atoms at a temperature of about 120 to 210° C. in an esterification zone using apparatus which permits water to be removed from the esterification zone to produce a carboxylate ester of 3-HOMeTHF and step (2) comprises heating the 3-HOMeTHF carboxylate ester in a pyrolysis zone at a temperature in the range of about 380 to 510° C. for a about 0.1 to 20 seconds to convert the ester compound to 3-methyleneTHF.

4. Process according to claim 1 wherein step (1) comprises contacting 3-HOMeTHF with a carboxylic acid containing 2 to 4 carbon atoms at a temperature of about 120 to 210° C. in an esterification zone using apparatus which permits water to be removed from the esterification zone to produce a carboxylate ester of 3-HOMeTHF; step (2) comprises heating the 3-HOMeTHF carboxylate ester in a pyrolysis zone at a temperature in the range of about 380 to 510° C. for a about 0.1 to 20 seconds to convert the ester compound to 3-methyleneTHF; and step (3) comprises contacting the 3-methyleneTHF with hydrogen at a temperature of 25 to 100° C. and a pressure in the range of about 1 to 50 bar absolute in the presence of a hydrogenation catalyst selected from chromium, rhenium, copper and the Group VIII metals to convert the 3-methyleneTHF to 3-MeTHF.

5. Process for the preparation of 3-methyltetrahydrofuran (3-MeTHF) by the steps comprising (1) contacting 3-(hydroxymethyl)tetrahydrofuran (3-HOMeTHF) with acetic acid at a temperature of about 120 to 210° C. in an esterification zone using apparatus which permits water to be removed from the esterification zone to produce 3-(acetoxymethyl)tetrahydrofuran (3-AcOMETHF); (2) heating the 3-AcOMETHF in a pyrolysis zone at a temperature in the range of about 380 to 510° C. for a about 1 to 10 seconds to convert the ester compound to 3-methyleneTHF; and (3) contacting the 3-methyleneTHF with hydrogen at a temperature of 25 to 100° C. and a pressure in the range of about 1 to 50 bar absolute in the presence of a hydrogenation catalyst selected from supported catalysts comprising about 1 to 10 weight percent palladium, platinum or rhodium deposited on a catalyst support material to convert the 3-methyleneTHF to 3-MeTHF.

6. Process according to claim 5 wherein step (1) is carried out using a reactive distillation apparatus comprising a distillation base pot and a distillation column wherein 3-HOMeTHF and acetic acid are fed to the reactive distillation apparatus, water is removed as a vapor from the upper section or top of the distillation column and a liquid mixture comprising 3-AcOMeTHF, acetic acid and 3-HOMeTHF is removed from the distillation base pot.

7. Process according to claim 5 wherein the 3-HOMeTHF used in step (1) is provided as a 10 to 90 weight percent solution in water obtained by contacting a solution comprising 10 to 90 weight percent 3-formyltetrahydrofuran in water with a nickel hydrogenation catalyst at a temperature of about 25 to 250° C. and a pressure of about 1 to 400 bar absolute.

8. Process according to claim 5 wherein the 3-HOMeTHF used in step (1) is provided as a 40 to 60 weight percent solution in water obtained by contacting a solution comprising 40 to 60 weight percent 3-formyltetrahydrofuran in water with a nickel hydrogenation catalyst selected from Raney nickel and supported nickel catalysts comprising about 20 to 80 weight percent nickel on a catalyst support material at a temperature in the range of about 90 to 150° C. and a pressure in the range of about 10 to 50 bar absolute.

9. Process for the preparation of 3-methyltetrahydrofuran (3-MeTHF) by the steps comprising (1) contacting an aqueous solution of 3-(hydroxy-methyl)tetrahydrofuran (3-HOMeTHF) with acetic acid in an esterification zone at a temperature of about 120 to 210° C. under reactive distillation conditions wherein water is removed as a vapor from the esterification zone and a mixture comprising 3-(acetoxymethyl)tetrahydrofuran (3-AcOMeTHF), 3-HOMeTHF and acetic acid is removed as a liquid from the esterification zone; (2) heating the liquid mixture from step (1) in a pyrolysis zone at a temperature in the range of about 380 to 510° C. for a about 1 to 10 seconds to convert the 3-AcOMeTHF to 3-methylenetetrahydrofuran (3-methyleneTHF)THF and condensing and recovering the 3-methyleneTHF as a solution in acetic acid; and (3) contacting the solution of 3-methyleneTHF in acetic acid with hydrogen in the presence of a hydrogenation catalyst under hydrogenation conditions of temperature and pressure to convert the 3-methyleneTHF to 3-methyltetrahydrofuran (3-MeTHF).

10. Process according to claim 9 wherein step (3) comprises contacting the 3-methyleneTHF with hydrogen at a temperature of 25 to 100° C. and a pressure in the range of about 1 to 50 bar absolute in the presence of a hydrogenation catalyst selected from supported catalysts comprising about 1 to 10 weight percent palladium, platinum or rhodium deposited on a catalyst support material.

11. Process according to claim 9 wherein the 3-HOMeTHF used in step (1) is provided as a 10 to 90 weight percent solution in water obtained by contacting a solution comprising 0.01 to 50 weight percent 3-formyltetrahydrofuran in an inert solvent with a nickel hydrogenation catalyst at a temperature of about 25 to 250° C. and a pressure of about 1 to 400 bar absolute using a 0.01 to 50 weight percent solution of 3-formyltetrahydrofuran in an inert solvent.

12. Process according to claim 9 wherein the 3-HOMeTHF used in step (1) is provided as a 40 to 60 weight percent solution in water obtained by contacting a solution comprising 0.1 to 10 weight percent 3-formyltetrahydrofuran in an inert solvent selected from water, 3-HOMeTHF, or a mixture thereof with a nickel hydrogenation catalyst selected from Raney nickel and supported nickel catalysts comprising about 20 to 80 weight percent nickel on a catalyst support material at a temperature in the range of about 90 to 150° C. and a pressure in the range of about 10 to 50 bar absolute.

* * * * *